United States Patent
Langston et al.

(10) Patent No.: US 9,622,669 B2
(45) Date of Patent: Apr. 18, 2017

(54) DIAGNOSIS OF NEURODEGENERATIVE DISORDERS

(75) Inventors: J. William Langston, Los Altos, CA (US); Ruksana Azhu Valappil, San Jose, CA (US)

(73) Assignee: PARKINSON'S INSTITUTE, Sunnyvale, CA (US)

( * ) Notice: Subject to any disclaimer, the term of this patent is extended or adjusted under 35 U.S.C. 154(b) by 460 days.

(21) Appl. No.: 12/997,767

(22) PCT Filed: Jun. 15, 2009

(86) PCT No.: PCT/US2009/047415
§ 371 (c)(1),
(2), (4) Date: Mar. 9, 2011

(87) PCT Pub. No.: WO2009/152521
PCT Pub. Date: Dec. 17, 2009

(65) Prior Publication Data
US 2011/0160603 A1    Jun. 30, 2011

Related U.S. Application Data

(60) Provisional application No. 61/061,553, filed on Jun. 13, 2008, provisional application No. 61/184,758, filed on Jun. 5, 2009.

(51) Int. Cl.
*A61B 5/024* (2006.01)
*A61B 5/0245* (2006.01)
*A61B 5/00* (2006.01)

(52) U.S. Cl.
CPC ........ *A61B 5/0245* (2013.01); *A61B 5/02405* (2013.01); *A61B 5/4011* (2013.01); *A61B 5/4035* (2013.01)

(58) Field of Classification Search
CPC .................. A61N 1/36025; A61B 5/02405
USPC ............. 600/508, 509, 544, 545; 607/45
See application file for complete search history.

(56) References Cited

U.S. PATENT DOCUMENTS

| | | | |
|---|---|---|---|
| 7,277,746 B2 | 10/2007 | Kuo et al. | |
| 2005/0177051 A1* | 8/2005 | Almen | A61B 5/02405 600/509 |
| 2006/0292565 A1* | 12/2006 | Small | C12Q 1/6883 435/6.11 |
| 2008/0194974 A1* | 8/2008 | Anders | A61B 5/02405 600/481 |

FOREIGN PATENT DOCUMENTS

| | | |
|---|---|---|
| EP | 1304072 A2 | 4/2003 |
| EP | 1304072 A3 | 1/2004 |
| WO | WO 2009/003147 | 12/2008 |

OTHER PUBLICATIONS

American Academy of Sleep Medicine. International Classification of sleep disorders, 2nd ed. Diagnostic and coding manual. American Academy of Sleep Medicine. Winchester IL 2005.

(Continued)

*Primary Examiner* — Allen Porter, Jr.
(74) *Attorney, Agent, or Firm* — Wilson Sonsini Goodrich & Rosati

(57) ABSTRACT

Methods are provided for non-invasive early screening of a subject for a neurodegenerative disorder, by analyzing one or more parameters associated with the neurodegenerative disorder.

9 Claims, 6 Drawing Sheets

(56) References Cited

OTHER PUBLICATIONS

Barbic, et al. Early Abnormalities of Vascular and Cardiac Autonomic Control in Parkinson's Disease Without Orthostatic Hypotension. 2007;49:21-2.
Becker, et al. Early diagnosis of Parkinson's disease. J Neurol. 2002;249(Suppl 3):III/40-III/48.
Berg. Biomarkers for the early detection of Parkinson's and Alzheimer's disease. Neurodegenerative Diseases. 2008;5:133-136.
Boeve, et al. Screening for REM sleep behavior disorder in patients with cognitive impairment and/or parkinsonism: Updated validation data on the Mayo Sleep Questionnaire. 2010.
Bonnet, et al. Heart Rate Variability in Insomaniacs and Matched Normal Sleepers. Psychosomatic Medicine. 1998;60:610-615.
Braak, et al. alpha-Sinuclein immunopositive Parkinson's disease related inclusion bodies in the lower brain stem nuclei. Acta Neuropathol (Berl). 2001;101:195-201.
Brennen, et al. Poincare plot interpretation using a physiological model of HRV based on a network of oscillators. Am J Physiol Heart Circ Circ Physiol. 2002;283:H1873-H1886.
Brodsky, et al. Heart rate variability as a biomarker for Parkinson's disease. (Abstract only). The MDS international conference. Jun. 8, 2009.
Fantini, et al. Olfactory deficit in idiopathic rapid eye movements sleep behavior disorder. Brain Research Bulletin. 2006;70:386-390.
Ferini-Strambi, et al. Cardiac Automatic Activity During Wakefulness and Sleep in REM Sleep Behavior Disorder. Sleep. 1996;19(5):367-369.
Ferini-Strambi, et al. REM sleep behaviour disorder. Neurol Sci. 2005;26:s186-s192.
Fujishiro, et al. Cardiac sympathetic denervation correlates with clinical and pathologic stages of Parkinson's disease. Mov. Disorders. 2008;epub ahead of print.
Goldstein, et al. Neurocirculatory abnormalities in PD with orthostatic hypotension: independent from levodopa treatment. Hypertension. 2005;46:1333-1339.
Haapaniemi, et al. Ambulatory ECG and analysis of heart rate variability in Parkinson's disease. J Neurol Neurosurg Psychiatry. Mar. 2001;70(3):305-10.
International search report and written opinion dated Feb. 12, 2010 for PCT Application No. US2009/047415.
Iwanaga, et al. Lewy body-type degeneration in cardiac plexus in Parkinson's and incidental Lewy body diseases. Neurology. 1999;52:1269-71.
Kallio, et al. Comparison of heart rate variability analysis methods in patients with Parkinson's disease. Med Biol Eng Comput. Jul. 2002;40(4):408-14.
Kallio, et al. Heart rate variability in patients with untreated PD. European J of Neurology. 2000;7:667-672.
Lanfranchi, et al. Cardiac autonomic regulation during sleep in idiopathic REM sleep behavior disorder. Sleep. Aug. 1, 2007;30(8):1019-25.
Langston, J. Can the electrocardiogram be used to identify premotor Parkinson's Disease? 2008.
Langston. The Parkinson's Complex: Parkinsonism is just the tip of the iceberg. Annals of Neurology. Apr. 2006; 59(4):591-596.
Li, et al. Progressive Loss of Cardiac Sympathetic Innervation in Parkinson's Disease. Annals of Neurology. 2002;52:220-223.
Malik. Heart rate variability: standards of measurement, physiological interpretation, and clinical use. Task Force of the European Society of Cardiology and the North American Society of Pacing and Electrophysiology. Circulation. Mar. 1, 1996;93(5):1043-65.
Miyamoto, et al. Three-year follow-up on the accumulation of cardiac 123I-MIBG scintigraphy in idiopathic REM sleep behavior disorder. Sleep Medicine. 2009.
Niskanen, et al. Software for advanced HRV analysis. Computer Methods and Programs in Biomedicine. Oct. 2004;76(1):73-81.
Oka, et al. Cardiovascular dysautonomia in de novo Parkinson's Disease. J Neurolog Sciences. 2006;241:59-65.
Olson, et al. Rapid eye movement Sleep Behavior Disorder: demographic, clinical and laboratory findings in 93 cases. Brain. 2000;123:331-339.
Orimo, et al. Reduced cardiac MIBG uptake is a potential biomarker for the presence of Lewy bodies. (Abstract only). The MDS international conference. Jun. 10, 2009.
Postuma, et al. Potential early markers of Parkinson disease in idiopathic REM sleep behavior disorder. Neurology. 2006;66:845-851.
Stiasny-Kolster, et al. Combination of 'idiopathic' REM sleep behaviour disorder and olfactory dysfunction as possible indicator for α-synucleinopathy demonstrated by dopamine transporter FP-CIT-SPECT. Brain. 2005; 128(1):126-137.
Strauss, H. Heart Rate Variability. Am J Physiol Regul Integr Comp Physiol. 2003;285:R927-931.
Takatsu, et al. Cardiac Sympathetic denervation from the early stage of PD: clinical and experimental studies with radiolabeled MIBG. J. Nuclear Medicine. 2000;41:71-77.
Turgut, et al. Asymmetry of sympathetic activity in a rat model of Parkinson's disease induced by 6-hydroxydopamine: haemodynamic, electrocardiographic and biochemical changes. Res Exp Med (Berl). 1998;197(5):281-92.
Valappil, et al. Can the EKG be used to identify prodromal PD? Assessment of heart rate variability during wakefulness in patients with RBD. 2010.
Wolters, et al. Parkinson's disease: premotor clinico-pathological correlations. J Neural Transm Suppl. 2006;(70):309-19.

* cited by examiner

DIAGNOSIS OF NEURODEGENERATIVE DISORDERS

CROSS-REFERENCE

This application claims the benefit of U.S. Provisional Application No. 61/061,553 filed Jun. 13, 2008 and U.S. Provisional Application No. 61/184,758, filed Jun. 5, 2009, which applications are incorporated herein by reference.

BACKGROUND OF THE INVENTION

Parkinson's disease (PD) is a progressive degenerative disease of the central and peripheral nervous systems. The risk of developing Parkinson's disease increases with age, and afflicted individuals are usually adults over 40. Parkinson's disease occurs in all parts of the world, and affects more than one million individuals in the United States alone. There are several other conditions that have the features of Parkinson's disease and are referred to as Parkinson's-like diseases. Both can be characterized by tremor, hypokinesia, rigidity, and postural instability.

The underlying causes of Parkinson's disease and Parkinson's-like diseases are numerous, and diagnosis can be complex. Parkinson's disease or Parkinson's-like disease is characterized by degeneration of dopaminergic neurons of the substantia nigra. The substantia nigra is a portion of the lower brain, or brain stem that helps control voluntary movements. The shortage of dopamine in the brain caused by the loss of these neurons may cause the observable disease symptoms.

There is a need for diagnosis and/or pre-motor diagnosis of Parkinson's disease or Parkinson's-like disease. Such diagnosis coupled with treatments alleviating symptoms or preventing further onset of symptoms would be beneficial. Currently there are a number of agents being tested to modify disease progression, as symptomatic treatments typically lead to unacceptable side-effects over time. Accordingly, means for screening subjects for Parkinson's disease or Parkinson's-like disease would be useful in insuring that appropriate treatments are promptly provided.

SUMMARY OF THE INVENTION

In one aspect, the present invention provides a method of screening a subject for Parkinson's disease or Parkinson's-like disease comprising: (a) obtaining an electrocardiogram (EKG) result from said subject; (b) comparing said EKG result to an EKG result range predetermined to be indicative of Parkinson's disease or Parkinson's-like disease; and (c) identifying said subject as suffering from or prone to Parkinson's disease or Parkinson's-like disease if said EKG result falls in said EKG result range.

In some embodiments, the EKG result comprises a heart rate variability (HRV) result. In some embodiments, the HRV result comprises a time domain measure. In some embodiments, the measure is selected from group consisting of standard deviation of R-R intervals (SDNN), the standard deviation of the heart rate (SDHR), the root mean square difference of successive RR intervals (RMSSD) and the percentage number of consecutive RR intervals differing by more than 50 msec (pNN50). In some embodiments, the HRV result comprises a geometric/non-linear measure. In some embodiments, the measure is selected from group consisting of short term HRV (SD1) and long term HRV (SD2) measured from Poincaré plots, the integral of density distribution (RR triangular index) and the triangular interpolation of NN (TINN). In some embodiments, the HRV result comprises a frequency domain measure. In some embodiments, the measure is selected from group consisting of very low frequency, VLF (0-0.04 Hz), low frequency, LF (0.04-0.15 Hz) and high frequency, HF (0.15-0.4 Hz), total power and LF/HF ratio.

In some embodiments, the subject is in a wakeful state or awake while obtaining the EKG result. In some embodiments, the EKG result is obtained for at least 1 minute, at least 2 minutes, at least 3 minutes, at least 5 minutes, at least 6 minutes, at least 7 minutes, at least 8 minutes, at least 9 minutes, at least 10 minutes, at least 15 minutes, at least 20 minutes, at least 3-5 minutes, at least 5-10 minutes, or at least 15-20 minutes. In some embodiments, the subject has been diagnosed with a REM sleep behavioral disorder (RBD). In some embodiments, the subject has a lower RMSSD than a subject not having an EKG result falling into an EKG result range predetermined to be indicative of Parkinson's disease or Parkinson's-like disease. In some embodiments, the subject has a lower pNN50 than a subject not having an EKG result falling into an EKG result range predetermined to be indicative of Parkinson's disease or Parkinson's-like disease. In some embodiments, the subject has a lower SDNN than a subject not having an EKG result falling into an EKG result range predetermined to be indicative of Parkinson's disease or Parkinson's-like disease. In some embodiments, the subject has a lower SD1 than a subject not having an EKG result falling into an EKG result range predetermined to be indicative of Parkinson's disease or Parkinson's-like disease. In some embodiments, the subject has a lower SD2 than a subject not having an EKG result falling into an EKG result range predetermined to be indicative of Parkinson's disease or Parkinson's-like disease. In some embodiments, the subject has a lower RR triangular index than a subject not having an EKG result falling into an EKG result range predetermined to be indicative of Parkinson's disease or Parkinson's-like disease. In some embodiments, the subject has a lower TINN than a subject not having an EKG result falling into an EKG result range predetermined to be indicative of Parkinson's disease or Parkinson's-like disease. In some embodiments, the subject has a lower VLF ($ms^2$) than a subject not having an EKG result falling into an EKG result range predetermined to be indicative of Parkinson's disease or Parkinson's-like disease. In some embodiments, the subject has a lower LF ($ms^2$) than a subject not having an EKG result falling into an EKG result range predetermined to be indicative of Parkinson's disease or Parkinson's-like disease. In some embodiments, the subject has a lower HF ($ms^2$) than a subject not having an EKG result falling into an EKG result range predetermined to be indicative of Parkinson's disease or Parkinson's-like disease. In some embodiments, the subject has a lower Total Power ($ms^2$) than a subject not having an EKG result falling into an EKG result range predetermined to be indicative of Parkinson's disease or Parkinson's-like disease. In some embodiments, the subject has a lower LF(nu) than a subject not having an EKG result falling into an EKG result range predetermined to be indicative of Parkinson's disease or Parkinson's-like disease. In some embodiments, the subject has a lower HF(nu) than a subject not having an EKG result falling into an EKG result range predetermined to be indicative of Parkinson's disease or Parkinson's-like disease. In some embodiments, the subject has a lower LF/HF ratio than a subject not having an EKG result falling into an EKG result range predetermined to be indicative of Parkinson's disease or Parkinson's-like disease. In some embodiments, the subject being screened has not been previously diagnosed as having Parkinson's disease or Parkinson's-like disease. In some embodiments, the subject does not exhibit any motor symptoms indicative of Parkinson's disease or Parkinson's-like disease. In some embodiments, the subject has been assessed to be 0 on the Hoehn and Yahr scale. In some embodiments, the subject has not been assessed on the Hoehn and Yahr scale. In some embodiments, the subject has been assessed to be 0 on the Unified Parkinson's Disease Rating Scale (UPDRS) scale. In some embodiments, the subject has not been assessed on the UPDRS scale. In some embodiments, the subject further has a symptom selected from the group consisting of constipation, olfactory dysfunction, psychological symptom, cognitive dysfunction, depression, sleep disorder, and RBD. In some embodiments, the subject further undergoes genetic testing for Parkinson's disease or Parkinson's-like disease or already has been identified as carrying a parkinsonogenic gene mutation. In some embodiments, the subject further undergoes cardiac imaging. In some embodiments, the subject undergoes Metaiodobenzylguanidine (MIBG) scintigraphy. In some embodiments, the subject further undergoes brain imaging. The brain imaging can include PET or MRI. In some embodiments, the subject is further considered for inclusion into a clinical trial. In some embodiments, the subject is prescribed a neuroprotective agent or therapy. The neuroprotective agent or therapy can be exercise, antioxidants, immunosuppressive calcineurin inhibitors, NOS inhibitors, sigma-1 modulators, AMPA antagonists, Ca2+ channel blockers, estrogen agonists, MAO-B inhibitors, kinase inhibitors, mitochondrial modulators or enhancers, alpha synuclein modulators, glycoprotein IIb/IIIa antagonists, erythropoietin, astaxanthin, boswellia, caffeine, curcumin, E vitamins, tocotrienols, flavonoids, naringenin, huperzine, or ubiquinol.

In another aspect, the present invention provides a method of diagnosing prodromal Parkinson's disease or Parkinson's-like disease comprising (a) measuring heart rate variability (HRV) of a subject; (b) comparing the HRV result of the subject to an HRV range predetermined to be indicative of Parkinson's disease or Parkinson's-like disease; and (c) diagnosing the subject as suffering from or prone to prodromal Parkinson's disease or Parkinson's-like disease if the HRV result of the subject falls in the HRV result range; wherein the subject has a symptom selected from the group consisting of REM sleep behavioral disorder (RBD), olfactory dysfunction, constipation, depression, cognitive deficits, very mild motor deficits suggestive of a motor disease or disorder, or a combination thereof.

In some embodiments, the HRV is measured by electrocardiogram (EKG). In some embodiments, the EKG result is obtained for at least 1 minute, at least 2 minutes, at least 3 minutes, at least 5 minutes, at least 6 minutes, at least 7 minutes, at least 8 minutes, at least 9 minutes, at least 10 minutes, at least 15 minutes, at least 20 minutes, at least 3-5 minutes, at least 5-10 minutes, or at least 15-20 minutes. In some embodiments, the HRV result comprises a time domain measure. In some embodiments, the measure is selected from group consisting of standard deviation of R-R intervals (SDNN), the standard deviation of the heart rate (SDHR), the root mean square difference of successive RR intervals (RMSSD) and the percentage number of consecutive RR intervals differing by more than 50 msec (pNN50). In some embodiments, the HRV result comprises a geometric/non-linear measure. In some embodiments, the measure is selected from group consisting of short term HRV (SD1) and long term HRV (SD2) measured from Poincaré plots, the integral of density distribution (RR triangular index) and the triangular interpolation of NN (TINN). In some embodiments, the HRV result comprises a frequency domain measure. In some embodiments, the measure is selected from group consisting of very low frequency, VLF (0-0.04 Hz), low frequency, LF (0.04-0.15 Hz) and high frequency, HF (0.15-0.4 Hz), total power and LF/HF ratio.

In some embodiments, the subject has a lower SDNN than a subject not having an EKG result falling into an EKG result range predetermined to be indicative of Parkinson's disease or Parkinson's-like disease. In some embodiments, the subject has a lower SD1 than a subject not having an EKG result falling into an EKG result range predetermined to be indicative of Parkinson's disease or Parkinson's-like disease. In some embodiments, the subject has a lower SD2 than a subject not having an EKG result falling into an EKG result range predetermined to be indicative of Parkinson's disease or Parkinson's-like disease. In some embodiments, the subject has a lower RR triangular index than a subject not having an EKG result falling into an EKG result range predetermined to be indicative of Parkinson's disease or Parkinson's-like disease. In some embodiments, the subject has a lower TINN than a subject not having an EKG result falling into an EKG result range predetermined to be indicative of Parkinson's disease or Parkinson's-like disease. In some embodiments, the subject has a lower VLF($ms^2$) than a subject not having an EKG result falling into an EKG result range predetermined to be indicative of Parkinson's disease or Parkinson's-like disease. In some embodiments, the subject has a lower LF($ms^2$) than a subject not having an EKG result falling into an EKG result range predetermined to be indicative of Parkinson's disease or Parkinson's-like disease. In some embodiments, the subject has a lower HF($ms^2$) than a subject not having an EKG result falling into an EKG result range predetermined to be indicative of Parkinson's disease or Parkinson's-like disease. In some embodiments, the subject has a lower Total Power ($ms^2$) than a subject not having an EKG result falling into an EKG result range predetermined to be indicative of Parkinson's disease or Parkinson's-like disease. In some embodiments, the subject has a lower LF(nu) than a subject not having an EKG result falling into an EKG result range predetermined to be indicative of Parkinson's disease or Parkinson's-like disease. In some embodiments, the subject has a lower HF(nu) than a subject not having an EKG result falling into an EKG result range predetermined to be indicative of Parkinson's disease, Parkinson's-like disease or prodromal Parkinson's disease. In some embodiments, the subject has a lower LF/HF ratio than a subject not having an EKG result falling into an EKG result range predetermined to be indicative of Parkinson's disease or Parkinson's-like disease. In some embodiments, the subject is in a wakeful state or awake while measuring the HRV. In some embodiments, the subject has been diagnosed with a REM sleep behavioral disorder (RBD). In some embodiments, the subject has a lower RMSSD than a subject not having an HPV result falling into the HPV result range predetermined to be indicative of Parkinson's disease or Parkinson's-like disease. In some embodiments, the subject has a lower pNN50 than a subject not having an HRV result falling into the HRV result range predetermined to be indicative of Parkinson's disease or Parkinson's-like disease. In some embodiments, the subject has not been previously diagnosed as having Parkinson's disease or Parkinson's-like disease. In some embodiments, the subject does not exhibit any motor symptoms indicative of Parkinson's disease or Parkinson's-like disease. In some embodiments, the subject has been assessed to be 0 on the Hoehn and Yahr scale. In some embodiments, the subject has not been assessed on the Hoehn and Yahr scale. In some embodiments, the subject has been assessed to be 0 on the Unified Parkinson's Disease Rating Scale (UPDRS) scale. In some embodiments, the subject has not been assessed on the UPDRS scale. In some embodiments, the subject further undergoes genetic testing for Parkinson's disease or Parkinson's-like disease or has already been tested for a genetic risk for Parkinson's disease or Parkinson's-like disease. In some embodiments, the subject further undergoes brain imaging. The brain imaging can be PET or MRI. In some embodiments, the subject is further considered for inclusion into a clinical trial. In some embodiments, the subject is prescribed a neuroprotective agent. In some embodiments, the neuroprotective agents are selected from the group consisting of antioxidants, immunosuppressive calcineurin inhibitor, NOS inhibitor, sigma-1 modulator, AMPA antagonist, Ca2+ channel blocker, estrogen agonist, glycoprotein IIb/IIIa antagonists, erythropoietin, astaxanthin, boswellia, caffeine, curcumin, E vitamins, tocotrienols, flavonoids, naringenin, huperzine and ubiquinol.

In another aspect, the present invention provides an algorithm for comparing the EKG result from a subject undergoing screening for Parkinson's disease or Parkinson's-like disease to an EKG result range predetermined to be indicative of Parkinson's disease, Parkinson's-like disease, or prodromal Parkinson's disease or Parkinson's-like disease. In some embodiments, the algorithm is used to determine if the EKG result from the subject falls in the EKG result range, thereby determining whether the subject is suffering from or prone to Parkinson's disease, Parkinson's-like disease, or prodromal Parkinson's disease or Parkinson's-like disease. In some embodiments, the algorithm is part of software.

In another aspect, the present invention provides a kit for carrying out the method of the present invention, the kit comprising reagents and instruments for measuring EKG of a subject undergoing screening for Parkinson's disease or Parkinson's-like disease. In some embodiments, the kit further comprises software for comparing the EKG result of the subject with an EKG result range predetermined to be indicative of Parkinson's disease or Parkinson's-like disease. In some embodiments, the kit further comprises instructions for use of the kit. In some embodiments, the kit further comprises a neuroprotective agent. In some embodiments, the kit further comprises material for olfactory testing. In some embodiments the test might include web-based tools for measuring HRV abnormalities.

In yet another aspect, the present invention provides a method for screening a subject for a neurodegenerative/neurological disorder comprising, obtaining data from a subject wherein said data are associated with one or more parameter related to said neurodegenerative/neurological disorder to produce an analysis result; comparing said analysis result to information from a control, wherein said information is predetermined to indicate absence of said neurodegenerative/neurological disorder. In some embodiments, the neurodegenerative/neurological disorder is selected from the group consisting of ADHD, Alzheimer's disease (AD), amyotrophic lateral sclerosis (ALS; Lou Gehrig's disease), Bell's Palsy, Cerebral Palsy, chemotherapy-induced neuropathies (e.g., from vincristine, paclitaxel, bortezomib), chorea-acanthocytosis, Creutzfeldt-Jakob Disease (CJD), progressive supranuclear palsy, corticobasal degeneration, fronto-temporal dementia, dementia, diabetes-induced neuropathies, diffuse Lewy body disease, Epilepsy, Essential Tremor, Friedreich's ataxia, Guillain-Barre Syndrome, Hemifacial Spasm, Huntington's disease (HD), Movement Disorders, Multiple Sclerosis, Multisystem Atrophy (MSA), Nervous System Tumors, Neurofibromatosis, Neuropathy, ocular diseases (ocular neuritis), Parkinson's disease (PD), Periodic Limb Movement Disorder, primary lateral sclerosis, Seizure Disorders, Tourette's Syndrome or Traumatic Brain Injury. In some embodiments, the parameter is selected from a group of parameters consisting of olfactory dysfunction, REM sleep behavioral disorder (RBD), constipation, depression, cognitive deficits, heart rate variability or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
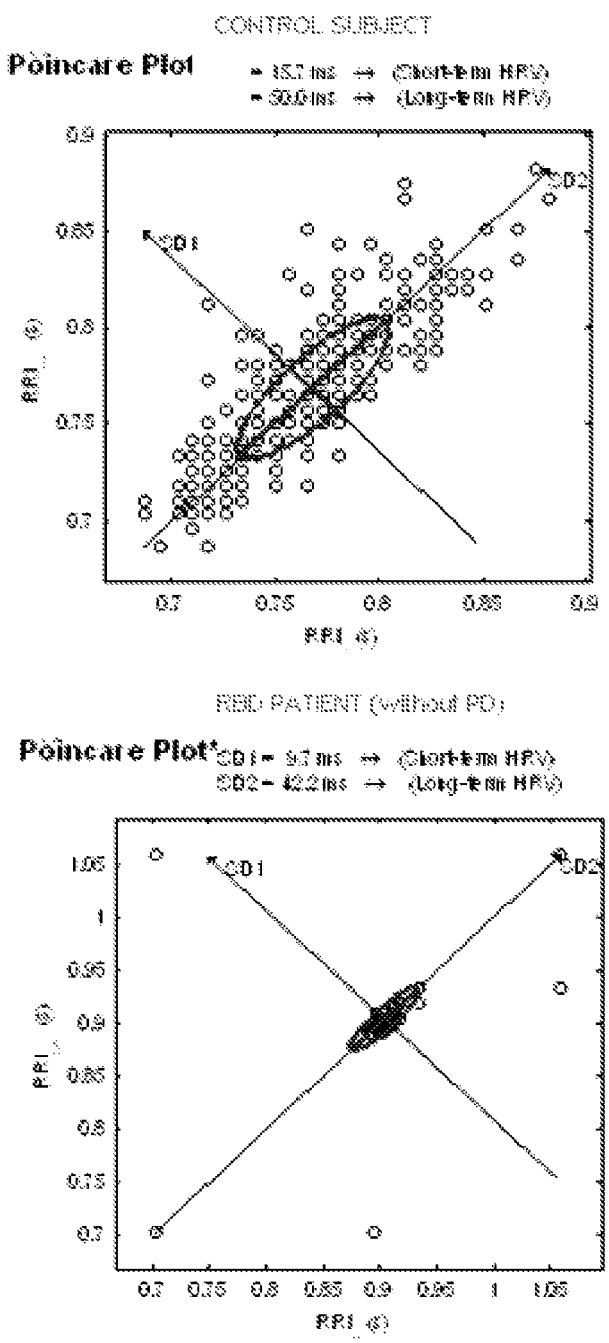
FIG. 1 depicts a scatter plot providing HRV analysis for a control and RBD subject.

In the present invention, methods are provided to screen a subject for a neurological or neurodegenerative disorder (used interchangeably herein). In one aspect, the present invention provides a method of screening a subject for Parkinson's disease or Parkinson's-like disease comprising (a) obtaining an electrocardiogram (EKG) result from the subject; (b) comparing the EKG result to an EKG result range predetermined to be indicative of Parkinson's disease or Parkinson's-like disease; and (c) identifying the subject as suffering from or prone to Parkinson's disease or Parkinson's-like disease if the EKG result falls in the EKG result range. In another aspect, the present invention provides a method for screening a subject for a neurodegenerative disorder comprising, (a) obtaining data from a subject wherein the data are associated with one or more parameter related to the disorder to produce an analysis result; (b) comparing the analysis result to information from a control, wherein the information is predetermined to indicate absence of the disorder.

Neurodegenerative diseases and disorders are a condition in which cells of the brain and/or spinal cord are lost. The brain and spinal cord are composed of neurons that p different functions such as controlling movements, processing sensory information, and making decisions. Cells of the brain and spinal cord are not readily regenerated en masse, so excessive damage can be devastating. Neurodegenerative diseases result from deterioration of neurons or their myelin sheath which over time will lead to dysfunction and disabilities. Neurodegenerative diseases are crudely divided into two groups according to phenotypic effects, although these are not mutually exclusive: conditions causing problems with movements, such as ataxia, and conditions affecting memory and related to dementia.

Parkinson's Disease

Parkinson's disease is a neurodegenerative disease. Many of the signs and symptoms associated with Parkinson's disease can precede typical Parkinson's disease, in some cases by many years. Involvement of the dopaminergic substantia nigra, which underlies the primary motor features of the disease, occurs at a time when the disease is well advanced at a neuropathological level, an observation that may account for the difficulties in successfully testing new drugs for potential disease modifying properties only after Parkinson's disease is evident. As a result, there is increasing interest in identifying pre-motor or prodromal signs and symptoms of Parkinson's disease in order to identify the disorder in its earliest stages, well before motor symptoms are in evidence. In one embodiment, a low-cost, non-invasive screening method is provided for pre-motor or prodromal Parkinson's disease. The motor features of Parkinson's disease are characterized by muscle rigidity, tremor, gait and postural abnormalities, a slowing of physical movement (bradykinesia) and, in extreme cases, a loss of physical movement (akinesia). The primary symptoms are the results of decreased stimulation of the motor cortex and other areas of the brain by the basal ganglia, normally caused by the insufficient formation and action of dopamine, which is produced in the dopaminergic neurons of the brain. The motor features of Parkinson's disease are just one component of a much more wide-spread disorder that causes an abundance of non-motor signs and symptoms, including olfactory dysfunction, REM sleep behavioral disorder (RBD), constipation, depression, and cognitive deficits. Importantly, many of these signs and symptoms can precede the motor symptoms by years to a decade or more.

Parkinson's-Like Diseases

There are several other conditions that have the features of Parkinson's disease and are interchangeably referred to as Parkinson's-like disease, secondary Parkinsonism, Parkinson's syndrome, or atypical Parkinson's. These are neurological syndromes that can be characterized by tremor, hypokinesia, rigidity, and postural instability. The underlying causes of Parkinson's-like disease are numerous, and diagnosis can be complex. A wide-range of etiologies can lead to a similar set of symptoms, including some toxins, a few metabolic diseases, and a handful of non-PD neurological conditions. A common cause is as a side effect of medications, mainly neuroleptic antipsychotics especially the phenothiazines (such as perphenazine and chlorpromazine), thioxanthenes (such as flupenthixol and zuclopenthixol) and butyrophenones (such as haloperidol (Haldol)), piperazines (such as ziprasidone), and rarely, antidepressants. Other causes include but are not limited to olivopontocerebellar degeneration, progressive supranuclear palsy, corticobasal degeneration, temporo-frontal dementia; drug induced like antipsychotics, prochlorperazine, metoclopromide; poisoning with carbon monoxide; head trauma; and Huntington's disease Parkinsonism. In some cases alpha-synucleinopathies can result in Parkinson's-like disease, secondary Parkinsonism, Parkinson's syndrome, or atypical Parkinson's. In a related embodiment the methods described herein are used to diagnose Parkinson's-like disease, secondary Parkinsonism, Parkinson's syndrome, atypical Parkinson's, or a alpha syncleinopathy.

Diagnosis or Risk of Neurodegenerative/Neurological Diseases and Disorders

A subject is an animal, including but not limited cows, horses, sheep, cats, dogs, pigs, horses, mice, rats, rabbits, squirrels, non-human primates, or humans. In various aspects, a subject is screened to determine if the subject is suffering from or prone to a neurological disorder such as Parkinson's disease. The screening methods comprise behavioral, biophysical, biochemical, and imaging assays and observations as well as questionnaires to determine if the subject is at risk for or is suffering from the early stages of a neurological disorder (e.g., Parkinson's disease). Biophysical and behavioral observations, such as physical examination of a subject for outward symptoms of disease can be evaluated independently, or combined with questionnaires and biochemical/imaging assays. Each individual assay can also be utilized independently or combined with biophysical evaluations or other tests that are known in the art and associated with a particular neurological disorder/disease. Examples of biochemical assays include genetic screens for mutations and/or polymorphisms (e.g., SNPs analysis, short tandem repeat analysis), biomarker-based assays, protein expression assays, immunohistochemistry assays or any combinations thereof. Material for biochemical assays can be sampled from all bodily fluids and tissues. Commonly employed bodily fluids include but are not limited to blood, serum, plasma, saliva, urine, gastric and digestive fluid, tears, stool, semen, vaginal fluid, interstitial fluids derived from tumorous tissue, and cerebrospinal fluid. Methods of obtaining samples of bodily tissue and fluids include but are not limited to biopsy, cheek swabbing, nose swabbing, rectal swabbing, skin fat extraction or other collection strategies for obtaining a biological or chemical substance.

In some embodiments, screening a subject will include imaging and scanning with the use of, but not limited to Positron Emission Tomography (PET) scans, Magnetic Resonance Imaging (MRI) scans, and Single-Photon Emission Computerized Tomography (SPECT) scans. Cardiovascular abnormalities related to Parkinson's disease in a subset of patients can be identified by heart rate spectral analysis.

In certain embodiments, a subject may be screened for early stage, development, or late-stage Parkinson's disease by screening for primary and secondary symptoms, as described herein immediately following. In other embodiments the subject may be screened for biochemical indications of disease e.g., genetic mutations and/or abnormal protein expression levels of genes and proteins, respectively, associated with a disorder, in some cases prior to any onset of symptoms such as changes in motor behavior.

Motor (primary) symptoms: There are various factors known in the art which are used to screen and diagnose a subject for various neurological disorders. For example, in one embodiment, a subject is examined to determine if the subject is suffering from Parkinson's disease by assessing presence of primary symptoms which include but are not limited to: bradykinesia, tremors, rigidity, impaired balance, or a change in gait.

Bradykinesia is slowness in voluntary movement. It produces difficulty initiating movement as well as difficulty completing movement once it is in progress. The delayed transmission of signals from the brain to the skeletal muscles, due to diminished dopamine, produces bradykinesia.

Tremors in the hands, fingers, forearm, or foot tend to occur when the limb is at rest but not when performing tasks. Tremor may occur in the mouth and chin as well.

Rigidity, or stiff muscles, may produce muscle pain and an expressionless, mask-like face. Rigidity tends to increase during movement.

Poor and impaired balance is due to the impairment or loss of the reflexes that adjust posture in order to maintain balance. Falls are common in people with Parkinson's.

Parkinsonian gait is the distinctive unsteady walk associated with Parkinson's disease. There is a tendency to lean unnaturally backward or forward, and to develop a stooped, head-down, shoulders-drooped stance. Arm swing is diminished or absent and people with Parkinson's tend to take small shuffling steps (called festination). Someone with Parkinson's may have trouble starting to walk, appear to be falling forward as they walk, freeze in mid-stride, and have difficulty making a turn.

In some embodiments, the Hoehn and Yahr staging is used in diagnosis of primary symptoms in a subject. The Hoehn and Yahr scale is a commonly used system for describing how the symptoms of Parkinson's disease progress (Hoehn M, Yahr M (1967). "Parkinsonism: onset, progression and mortality" Neurology 17 (5): 427-42). The scale allocates stages from 0 to 5 to indicate the relative level of disability.

Stage 1: Symptoms on one side of the body only.
Stage 2: Symptoms on both sides of the body. No impairment of balance.
Stage 3: Balance impairment. Mild to moderate disease. Physically independent.
Stage 4: Severe disability, but still able to walk or stand unassisted.
Stage 5: Wheelchair-bound or bedridden unless assisted.

In other embodiments, the Unified Parkinson's Disease Rating Scale (UPDRS) is used in the diagnosis of a subject. The UPDRS is a rating tool to follow the course of Parkinson's disease. It is made up of the 1) Mentation, Behavior, and Mood, 2) Activities of Daily Living and 3) Motor sections. These are evaluated by interview. Some sections require multiple grades assigned to each extremity. A total of 199 points are possible. 199 represents the worst (total) disability), 0—no disability.

In other embodiments, the Schwab and England Activities of Daily Living assessment can be used in the diagnosis of a subject. The subject is assigned a rating from 0% to 100%. Rating can be assigned by rater or by subject.

Non-motor (secondary) symptoms: In some embodiments, progressive loss of voluntary and involuntary muscle control produces a number of secondary symptoms associated with Parkinson's disease. In some embodiments these symptoms are indicative of onset of primary symptoms. In other embodiments secondary symptoms can be in the absence of diagnosable motor symptoms, or present with primary symptoms. These symptoms can develop well before, shortly before, during, or after the onset and development of primary symptoms. In some cases, a subject can experience and display these symptoms about 50, 40, 30, 20, 15, 10, 5, 2 years, 1 year or 6 months before or 6 months, 1, 2, 5, 10, 15, 20, 30, 40, or more years after onset and display of primary symptoms. Some patients develop these secondary symptoms well before, years before the patients develop primary symptoms characteristic with a disorder. Some secondary symptoms of Parkinson's disease include but are not limited to the following: Constipation occurring in a subject's 20's, 30's 40's or 50's; difficulty swallowing (dysphagia), saliva and food that collects in the mouth or back of the throat may cause choking, coughing, or drooling; excessive salivation (hypersalivation), excessive sweating (hyperhidrosis), loss of bladder and/or bowel control (incontinence); loss of sense of smell, olfactory dysfunction (anosmia); rapid eye movement (REM) sleep behavior disorder and other sleep disorders; changes in the cardiac sympathetic denervation, changes in the sympathetic innervation of the heart; loss of intellectual capacity (dementia), psychosocial: anxiety, depression, isolation; scaling, dry skin on the face and scalp (seborrhea); slow response to questions (bradyphrenia); small, cramped handwriting (micrographia); soft, whispery voice (hypophonia), and fatigue.

Therefore, in certain embodiments, diagnosis is based on symptoms and ruling out other disorders that produce similar symptoms. However to make a diagnosis of typical Parkinson's disease, a subject must have two or more of the diagnosable motor symptoms, one of which is a resting tremor or bradykinesia. In many cases, this diagnosis is made after observing that symptoms have developed and become established over a period of time. Such diagnostic techniques described above are known in the art.

After a thorough neurological exam and medical history, the neurologist may order computerized tomography (CT scan) or magnetic resonance imaging (MRI scan) to meet the other criterion for a diagnosis of Parkinson's disease: ruling out disorders (e.g., brain tumor, stroke) that produce Parkinson's-like symptoms. Some examples follow: medications—antipsychotics (e.g., Haldol) and anti-emetics (e.g., Compazine); multiple strokes; hydrocephalus; progressive supranuclear palsy—degeneration of midbrain structures; Shy-Drager syndrome—atrophy of central and sympathetic nervous systems; Wilson's disease—copper excretion causes degeneration of the liver and basal ganglia; Blood and/or cerebrospinal fluid (CSF) analysis may be ordered to look for specific abnormalities associated with other disorders.

In some embodiments, diagnosis is based on secondary non-motor symptoms even when the subject show no or very few of the primary motor symptoms associated with the neurological disease.

In some embodiments, the secondary symptom or non-motor is selected from the group consisting of rapid eye movement sleep behavioral disorder, olfactory dysfunction, cardiac sympathetic denervation, constipation, depression, anxiety and dementia. In some embodiments, the secondary symptom is a sleep disorder.

Therefore, where primary and secondary symptoms are insufficient to indicate disease onset, a genetic/biochemical or other type of screen can be conducted to determine if the subject is at risk for developing a neurological disorder (e.g., Parkinson's disease or Alzheimer's disease).

Heart Rate Variability (HRV) in Prodromal/Pre-Motor Parkinson's Disease or Parkinson's-Like Disease In one embodiment, the present invention provides a method of assessing whether a population of patients has prodromal/pre-symptomatic/pre-motor Parkinson's disease or Parkinson's-like disease. In some embodiments, the patients present with a REM sleep behavior disorder (RBD). In some embodiments, REM sleep behavior disorder (RBD) with no obvious evidence of Parkinson's disease or Parkinson's-like disease or dementia with Lewy bodies (DLB) is studied. RBD is a parasomnia with loss of muscle atonia during REM sleep resulting in enactment of dreams (Ferini-Strambi et al and Olson et al.) and is associated with alpha-synucleinopathies (Olson et al., Stiasny-Kolster et al. Boeve et al) such as Parkinson's disease or Parkinson's-like disease, Dementia with Lewy Bodies (DLB) and Multiple System Atrophy (MSA). RBD may precede and predict the clinical symptoms of typical Parkinson's disease or Parkinson's-like disease by years to a decade or more. Up to 65% of patients with pure RBD will eventually develop Parkinson's disease, Parkinson's-like disease, or a related synucleinopathy.

Subjects with REM sleep behavioral disorder (RBD) can have significant alterations in heart rate variability (HRV) as measured by electrocardiogram tracings compared to a group of age matched controls without RBD. In some embodiments, EKG is used to identify changes in HRV in individuals with RBD with possible "pre-motor" or prodromal Parkinson's disease or Parkinson's-like disease. In some embodiments, a routine EKG is used as a simple, non-invasive, and low-cost screening tool for pre-motor/prodromal Parkinson's disease or Parkinson's-like disease that can be incorporated into routine physical examinations of individuals. In some embodiments, the individuals going through the physical examination with a routine EKG for screening pre-motor Parkinson's disease or Parkinson's-like disease are in the 50s and beyond. In some embodiments, Lewy bodies have been observed in the superior sympathetic ganglia at least 10 years before the diagnosis of Parkinson's disease or Parkinson's-like disease. Furthermore, cardiac Lewy neuritic pathology has been found in most if not all cases of incidental Lewy body cases (presumable Braak Stage I and II Parkinson's disease or prodromal Parkinson's disease).

In some embodiments, the EKG result comprises a heart rate variability (HRV) result. The HRV result may comprise a time domain measure. The measure can be selected from the group consisting of standard deviation of R-R intervals (SDNN), the standard deviation of the heart rate (SDHR), the root mean square difference of successive RR intervals (RMSSD), and the percentage number of consecutive RR intervals differing by more than 50 msec (pNN50). In some embodiments, the EKG result is obtained for at least 1 minute, at least 2 minutes, at least 3 minutes, at least 5 minutes, at least 6 minutes, at least 7 minutes, at least 8 minutes, at least 9 minutes, at least 10 minutes, at least 15 minutes, at least 20 minutes, at least 3-5 minutes, at least 5-10 minutes, or at least 15-20 minutes.

In some embodiments, the HRV result comprises a geometric/non-linear measure. These include measures derived from the Poincaré plot, which is a graphical representation of the relationship between consecutive RR intervals, where an RR interval is plotted against the preceding RR interval. The short term HRV (beat-to-beat) is calculated perpendicular to the line of identity (SD1) and the long term (overall HRV) is calculated along the line of identity (SD2). Geometric measures include RR triangular index and the triangular interpolation of NN (TINN).

In some embodiments, the HRV result comprises a frequency domain measure, e.g., Very Low Frequency (VLF) (0-0.04 Hz), Low Frequency (LF) (0.04-0.15 Hz), or High Frequency (HF) (0.15-0.4 Hz). The values can be reported in both absolute values and normalized units. In some embodiments, the frequency domain measures include Total Power and the LF/HF ratio.

In another aspect, the present invention provides a method for screening a subject for a neurological disorder comprising, (a) obtaining data from a subject wherein the data are associated with one or more parameter related to the neurological disorder to produce an analysis result; (b) comparing the analysis result to information from a control, wherein the information is predetermined to indicate absence of the neurological disorder.

In another aspect, the present invention provides a method of screening a subject for Parkinson's disease or Parkinson's-like disease by measuring cardiac autonomic denervation as one pathway to achieve large scale screening of the general population for Parkinson's disease or Parkinson's-like disease. Cardiac autonomic denervation (CAD) is a near universal feature in Parkinson's disease or Parkinson's-like disease when the motor signs are fully evident. Additionally, CAD may precede motor dysfunction in Parkinson's disease or Parkinson's-like disease as suggested by the presence of Lewy bodies in the superior sympathetic ganglia many years prior to diagnostic Parkinson's disease and in the cardiac plexus in 100% of Parkinson's and incidental Lewy body disease cases. CAD results in reduced HRV and is documented in patients with clinically diagnosable Parkinson's disease. In one embodiment, an easy, non-invasive method of measuring CAD is by heart rate variability (HRV), which can be assessed using a standard electrocardiogram (EKG). Since patients with pre-motor/prodromal Parkinson's disease and/or Parkinson's-like disease may have CAD, this abnormality can be identified by measuring HRV. In some embodiments, HRV is used as a marker to assess RBD. HRV can be measured during wakefulness or during sleep.

In one embodiment, cardiac sympathetic denervation (CSD), a feature in Parkinson's disease, is observed in presymptomatic Parkinson's disease and/or Parkinson's-like disease. In some embodiments, CSD is observed using imaging agents including but not limited to iodine-123 metaiodobenzylguanidine and fluorodopa positron emission tomography imaging and by cardiac catheterization. CSD reduces heart rate variability (HRV), which can be assessed using a standard electrocardiogram (EKG). Reduced HRV is observed in patients with already diagnosed Parkinson's disease. CSD is documented by assessing changes in HRV in a population that has a high probability of having pre-motor Parkinson's disease or Parkinson's-like disease, i.e., patients with RBD. In some embodiments, the present invention's screening method for pre-motor/prodromal Parkinson's disease or Parkinson's-like disease is incorporated into annual physical examinations.

In other embodiments of the invention, other non-motor features of Parkinson's disease or Parkinson's-like disease are analyzed, including testing of changes in sense of smell and evaluation for other features such as autonomic dysfunction, and changes in mood and cognition. Therefore, in re-evaluation of all RBD patients for other features of Parkinson's disease or Parkinson's-like disease, individuals who have subsequently developed Parkinson's disease or Parkinson's-like disease are identified, thereby providing supporting evidence that they had pre-motor/prodromal Parkinson's disease or Parkinson's-like disease at the time of their sleep recordings.

In some embodiments, the subject of the present invention is in a wakeful state or awake while obtaining the EKG result. In some embodiments, the subject has been diagnosed with a REM sleep behavioral disorder (RBD). In some embodiments, the HRV result comprises a frequency domain measure, e.g., Very Low Frequency (VLF) (0-0.04 Hz), Low Frequency (LF) (0.04-0.15 Hz), or High Frequency (HF) (0.15-0.4 Hz). The values can be reported in both absolute values and normalized units. In some embodiments, the frequency domain measures include Total Power and the LF/HF ratio. In some embodiments, the subject has a lower RMSSD than a subject not having an EKG result falling into an EKG result range predetermined to be indicative of Parkinson's disease or Parkinson's-like disease. In some embodiments, the subject has a lower pNN50 than a subject without having an EKG result falling into an EKG result range predetermined to be indicative of Parkinson's disease or Parkinson's-like disease. In some embodiments, the subject has a lower SDNN than a subject without having an EKG result falling into an EKG result range predetermined to be indicative of Parkinson's disease or Parkinson's-like disease. In some embodiments, the subject has a lower SD1 than a subject without having an EKG result falling into an EKG result range predetermined to be indicative of Parkinson's disease or Parkinson's-like disease. In some embodiments, the subject has a lower SD2 than a subject without having an EKG result falling into an EKG result range predetermined to be indicative of Parkinson's disease or Parkinson's-like disease. In some embodiments, the subject has a lower RR triangular index than a subject without having an EKG result falling into an EKG result range predetermined to be indicative of Parkinson's disease or Parkinson's-like disease. In some embodiments, the subject has a lower TINN number than a subject without having an EKG result falling into an EKG result range predetermined to be indicative of Parkinson's disease or Parkinson's-like disease. In some embodiments, the subject has a lower $VLF(ms^2)$ than a subject without having an EKG result falling into an EKG result range predetermined to be indicative of Parkinson's disease or Parkinson's-like disease. In some embodiments, the subject has a lower $LF(ms^2)$ than a subject without having an EKG result falling into an EKG result range predetermined to be indicative of Parkinson's disease or Parkinson's-like disease. In some embodiments, the subject has a lower $HF(ms^2)$ than a subject without having an EKG result falling into an EKG result range predetermined to be indicative of Parkinson's disease or Parkinson's-like disease. In some embodiments, the subject has a lower Total $Power(ms^2)$ than a subject without having an EKG result falling into an EKG result range predetermined to be indicative of Parkinson's disease or Parkinson's-like disease. In some embodiments, the subject being screened by the method of the present invention has not been previously diagnosed as having Parkinson's disease or Parkinson's-like disease. In some embodiments, the subject does not exhibit any motor symptoms indicative of Parkinson's disease or Parkinson's-like disease. In some embodiments, the subject has been assessed to be 0 on the Hoehn and Yahr scale. In some embodiments, the subject has not been assessed on the Hoehn and Yahr scale. In some embodiments, the subject has been assessed to be 0 on the Unified Parkinson's disease rating scale (UPDRS). In some embodiments, the subject has not been assessed on the UPDRS scale. In some embodiments, the subject further has a symptom including but not limited to constipation, olfactory dysfunctions, autonomic disturbances such as dysautonomia, psychological symptoms such as depression, and sleep disorders such as RBD. In some embodiments, the subject further undergoes genetic testing for Parkinson's disease or Parkinson's-like disease. In some embodiments, the subject further undergoes brain imaging. The brain imaging can be PET or MRI. In some embodiments, the subject is considered for inclusion into a clinical trial. In some embodiments, the subject is prescribed a neuroprotective agent or therapy. One therapy to prevent or delay onset of Parkinson's disease or Parkinson's-like disease is exercise. Some neuroprotective therapies offer protection against cell degeneration to the neuronal cells. Other neuroprotective agents specifically protect the dopamine neurons. The majority of neuroprotective agents are antioxidants. An immunosuppressive calcineurin inhibitor, NOS inhibitor, sigma-1 modulator, AMPA antagonist and Ca2+ channel blocker have all shown neuroprotective activity. An estrogen agonist and two glycoprotein IIb/IIIa antagonists also exhibit neuroprotective activity. Neuroprotective agents that can be used in the present invention include but are not limited to erythropoietin, astaxanthin, boswellia, caffeine, curcumin, E vitamins as tocotrienols, flavonoids, grapefruit juice (naringenin), huperzine and ubiquinol. Other disease modifying agents such as MAO inhibitors, calcium channel blockers, kinase inhibitors, mitochondrial modulators/enhancers, alpha synuclein modulators can be used in the methods described herein.

It will be evident, that various risk factors known for a neurological disorder can be utilized to screen a subject, in order to determine whether the subject is at risk of developing the particular neurological disorder. Therefore, in various embodiments, such neurological disorders include, but are not limited to, ADHD, Alzheimer's disease (AD), amyotrophic lateral sclerosis (ALS; Lou Gehrig's disease), Bell's Palsy, Cerebral Palsy, chemotherapy-induced neuropathies (e.g., from vincristine, paclitaxel, bortezomib), chorea-acanthocytosis, Creutzfeldt-Jakob Disease (CJD), progressive supranuclear palsy, corticobasal degeneration, fronto-temporal dementia, dementia, diabetes-induced neuropathies, diffuse Lewy body disease, Epilepsy, Essential Tremor, Friedreich's ataxia, Guillain-Barre Syndrome, Hemifacial Spasm, Huntington's disease (HD), Movement Disorders, Multiple Sclerosis, Multisystem Atrophy (MSA), Nervous System Tumors, Neurofibromatosis, Neuropathy, ocular diseases (ocular neuritis), Parkinson's disease (PD), Periodic Limb Movement Disorder, primary lateral sclerosis, Seizure Disorders, Tourette's Syndrome or Traumatic Brain Injury. In some embodiments, a subject is at risk of developing or is suffering from Parkinson's disease or Parkinson's-like disease, Alzheimer's Disease or a Neuropathy. In other embodiments, a subject is suffering from the early stages of Parkinson's disease or Parkinson's-like disease, Alzheimer's Disease or a Neuropathy.

In some embodiments, the parameters related to the neurological disorders include but are not limited to olfactory dysfunction, REM sleep behavioral disorder (RBD), constipation, depression, cognitive deficits, heart rate variability or a combination thereof.

In another aspect, the present invention provides an algorithm for comparing the EKG result from a subject undergoing the screening for Parkinson's disease or Parkinson's-like disease to an EKG result range predetermined to be indicative of Parkinson's disease or Parkinson's-like disease. The algorithm can be used to determine if the EKG result from the subject falls in the EKG result range, thereby determining whether the subject is suffering from or prone to Parkinson's disease or Parkinson's-like disease.

In yet another aspect, the present invention provides kits for carrying out the method of the present invention. The kit may include materials to test for the predisposition of a neurological disorder, e.g. Parkinson's disease or Parkinson's-like disease. In some embodiments, the kits include reagents and instruments for measuring EKG of a subject undergoing the screening for Parkinson's disease or Parkinson's-like disease. The kits further comprise suitable packaging, and written material that can include instructions for use, discussion of clinical studies, listing of side effects, and the like. The kit may further contain a neuroprotective agent. The kit may further include material for olfactory testing. In some embodiments, the reagents, instruments and the other agents are provided as separate compositions in separate containers within the kit.

Genetic Screening

As indicated herein above, screening a subject to determine if the subject is at-risk for developing a neurological disorder such as Parkinson's disease or Parkinson's-like disease can be based on imaging, behavior, biophysical and/or biochemical screening for traits/factors associated with a neurological disorder/disease. In one such aspect of the invention, a biochemical screening involves genetic testing. Therefore, in various embodiments of the invention, a method of treating a subject at risk of a neurological disorder comprises screening genetic material from the subject to determine if markers are present (e.g., mutations of genes, expression levels of proteins) associated with the neurological disorder or pre-motor/prodromal symptoms of the disorder, thereby determining risk, and administering a compound (or a combination of two or more compounds) that inhibits, decreases, reverses, or prevents α-synuclein fibrillation and/or aggregation, or induces kinase inhibition, or induces MAO inhibition, or acts as a calcium channel blocker, or as a mitochondrial enhancer to the subject to delay or reduce progression of a neurological disorder. The disorder may be at the early onset stage or the subject may be entirely asymptomatic. For example, to determine if a subject is at risk for Parkinson's disease, the subject can be screened for mutations of one or more LRRK2, α-synuclein, parkin gene or a combination of two or more markers thereof. Furthermore, the subject can be screened for elevated expression levels of a protein indicative of disease onset or risk for disease. Methods of performing such genetic/biochemical screens are known in the art.

In some embodiments, the subject is screened for a mutation in a gene selected from the group consisting of leucine-rich repeat kinase 2 (LRRK2), α-synuclein (SNCA), parkin (PRKN), ubiquitin C-terminal hydrolase L1 (UCH-L1), oncogene DJ-1 gene, PTEN-induced protein kinase 1 (PINK1), and microtubule-associated protein tau (MAPT). Such mutations include but are not limited to substitution, deletion, insertion, duplication, triplication or a combination thereof.

LRRK2. In one embodiment, the subject is pre-symptomatic of primary symptoms for Parkinson's disease, but genetic screening yields information on the presence mutations and/or polymorphisms of one or more genes associated with Parkinson's disease. For example, a subject is screened for the prevalence of two common leucine-rich repeat kinase 2 (LRRK2) gene mutations. Patients with LRRK2 mutations have shown typical levodopa responsive Parkinson's disease with tremor being the most common presenting feature. Patients with the G2019S mutation have shown a similar age of onset of symptoms when compared with patients with other LRRK2 mutations or sporadic Parkinson's disease, and can be more likely to have a family history of Parkinson's disease. In addition, a familial A1442P (4,324 G>C) mutation has been observed. Therefore, in one embodiment, a subject is tested to determine the presence of LRRK2 mutations and if positive for such mutations, the subject is administered one or more therapies that inhibit, decrease, reverse, or prevents α-synuclein fibrillation and/or aggregation, inhibits MAO, inhibits kinases, blocks calcium channels, enhances mitochondrial function as a prophylactic to delay, reduce or eliminate Parkinson's disease onset or progression.

α-synuclein. In other embodiments, genetic screens detect the presence of α-synuclein gene mutations or multiplications and/or polymorphisms which are major underlying genetic defects known in familial juvenile onset Parkinson's disease, and α-synuclein is a major constituent of Lewy Bodies, the pathological hallmark of Parkinson's disease.

Mutations in, or over-expression of, α-synuclein may cause damage by interfering with particular steps of neuronal membrane traffic. α-synuclein selectively blocks endoplamic reticulum (ER)-to-Golgi transport, thus causing ER stress. α-synuclein may serve a chaperone function for the proper folding of soluble NSF attachment receptor (SNAREs) that are important for neurotransmitter release.

Therefore in some embodiments, a subject is diagnosed or pronounced to be at-risk after a genetic screen to determine the presence of α-synuclein mutations and/or polymorphisms and/or detection of elevated expression levels of α-synuclein, wherein mutations and/or polymorphisms and/or elevated expression levels are indicative of risk of Parkinson's disease. Further, the subject may be optionally examined for display of one or more secondary symptoms. Thus, in one such embodiment, the subject is administered one or more therapies that inhibit, decrease, reverse, or prevent α-synuclein aggregation and fibrillation and/or aggregation, or inhibits kinases such as LRRK kinase, or inhibits MAO, or acts as a calcium channel blocker, or a mitochondrial enhancer as a prophylactic to delay, reduce or eliminate Parkinson's disease and/or Parkinson's-like disease onset or progression.

In another embodiment, a subject is screened for LRRK2 mutations described above and α-synuclein mutations and/or polymorphisms and/or overexpression, where positive results (e.g., mutations, overexpression) are indicative of risk of developing Parkinson's Disease, and the subject is treated with one or more therapies that inhibit, decrease, reverse, or prevents α-synuclein fibrillation and/or aggregation or inhibits kinases such as LRRK kinase, or inhibits MAO, or acts as a calcium channel blocker, or a mitochondrial enhancer as a prophylactic to delay, reduce or eliminate Parkinson's disease and/or Parkinson's-like disease onset or progression.

Parkin gene. In another embodiment, a subject is genetically screened to determine if one or more parkin gene mutation and/or polymorphism is present to determine risk for Parkinson's Disease. If one or more parkin gene(s) are mutated or have a polymorphism associated with a neurological disease then the subject can be treated with a compound named herein. People with one mutation may develop the disease 12 years earlier than average. Two mutated genes are linked with disease which starts 13 years earlier. The prevalence of Parkinson's increases with age—appearing in 1% of people over 60 and 4-5% of those over 85—but it can develop in much younger patients. Inheriting mutations, deletions, or multiplications of the parkin gene is associated with the development of early-onset Parkinson's—which refers to disease which appears before the age of 50.

Therefore, in prophylactic treatment methods of the invention, a subject undergoes genetic screen to determine risk for Parkinson's disease (e.g., presence of one or two PRKN mutations) and if found to be at-risk, is administered one or more compound that inhibits, decreases, reverses, or prevents α-synuclein fibrillation and/or aggregation. In some further embodiments, a subject may be screened for PRKN and LRRK2 mutations and/or polymorphisms to determine if a prophylactic administration of one or more therapies described herein that inhibits, decreases, reverses, or prevents α-synuclein fibrillation and/or aggregation, or inhibits kinases such as LRRK kinase, or inhibits MAO, or acts as a calcium channel blocker, or a mitochondrial enhancer as a prophylactic to delay, reduce or eliminate Parkinson's disease and/or Parkinson's-like disease onset or progression is desirable. In any of the genetic screens described herein, the presence of mutations and/or polymorphisms in one familial gene should not serve as exclusion criteria in a screen for further genetic variation.

In certain embodiments, a subject may be routinely screened for mutations and/or polymorphisms, to determine if at risk and determine if a prophylactic administration of one or more compounds described herein that inhibits, decreases, reverses, or prevents α-synuclein fibrillation and/or aggregation, or inhibits kinases such as LRRK kinase, or inhibits MAO, or acts as a calcium channel blocker, or a mitochondrial enhancer as a prophylactic to delay, reduce or eliminate Parkinson's disease and/or Parkinson's-like disease onset or progression is desirable. In other embodiments, a subject may be first screened and secondary non-motor symptoms identified, determined to be at risk, and further screened for mutations and/or polymorphisms to determine if a prophylactic administration of one or more therapies described herein that inhibits, decreases, reverses, or prevents α-synuclein fibrillation and/or aggregation, or inhibits kinases such as LRRK kinase, or inhibits MAO, or acts as a calcium channel blocker, or a mitochondrial enhancer as a prophylactic to delay, reduce or eliminate Parkinson's disease and/or Parkinson's-like disease onset or progression is desirable.

Parkinson's Disease or Parkinson's-Like Disease Therapies

Parkinson's disease is a chronic disorder for which no cure is currently known and existing medications and therapies provide transient relief from the primary motor-related symptoms but may not always be disease modifying.

Levodopa (L-dopa) is used as a form of symptomatic treatment. L-dopa is transformed into dopamine in the dopaminergic neurons by L-aromatic amino acid decarboxylase. However, only 1-5% of L-dopa enters the dopaminergic neurons. The remaining L-dopa is often metabolized to dopamine elsewhere, causing a wide variety of side effects. Due to feedback inhibition, L-dopa results in a reduction in the endogenous formation of L-dopa, and so eventually becomes counterproductive. Carbidopa and benserazide are dopa decarboxylase inhibitors. They help to prevent the metabolism of L-dopa before it reaches the dopaminergic neurons and are generally given as combination preparations of carbidopa/levodopa (co-careldopa) and benserazide/levodopa (co-beneldopa). Duodopa is a combination of levodopa and carbidopa.

The dopamine agonists bromocriptine, pergolide, pramipexole, ropinirole, cabergoline, apomorphine, and lisuride are moderately but only transiently effective when utilized for symptomatic treatment. Dopamine agonists can be useful for patients experiencing on-off fluctuations and dyskinesias as a result of high doses of L-dopa.

MAO-B inhibitors (first, second, or later generation MAO-B inhibitors) reduce the symptoms associated with Parkinson's disease by inhibiting the breakdown of dopamine secreted by the dopaminergic neurons. An exemplary MAO-B inhibitor is Rasagiline [N-propargyl-1(R)-aminoindan], a second-generation propargylamine pharmacophore that selectively and irreversibly inhibits brain MAO-B.

Noradrenergic drugs such as norepinephrine may be useful in preventing, reversing, or treating early premotor/prodromal Parkinson's disease or Parkinson's-like disease.

Kinase inhibitors such as p38 mitogen-activated protein kinase inhibitors, mixed lineage kinase inhibitors, (for example CEP-1347), Leucine-rich Repeat Kinase 2 (LRRK2) inhibitors may be useful in preventing, reversing, or treating early premotor/prodromal Parkinson's disease or Parkinson's-like disease.

Mitochondrial modulators such as Enzyme co-Q10 may be useful in preventing, reversing, or treating early premotor/prodromal Parkinson's disease or Parkinson's-like disease.

Calcium channel blockers such as isradipine may be useful in preventing, reversing, or treating early premotor/prodromal Parkinson's disease or Parkinson's-like disease.

Increased exercise may be useful in preventing, reversing, or treating early premotor/prodromal Parkinson's disease or Parkinson's-like disease.

Compounds that prevent/reverse/disaggregate, halt aggregation of alpha-synuclein may be useful in preventing, reversing, or treating early premotor/prodromal Parkinson's disease or Parkinson's-like disease. Such compounds are described and listed in WO/2009/003147, the publication is hereby incorporated in its entirety.

In some embodiments, a subject who has been diagnosed to have prodromal or pre-motor Parkinson's disease or Parkinson's-like disease using the method of the present invention can be treated with a prophylactic drug or other therapy such as exercise. A prophylactic drug for Parkinson's disease or Parkinson's-like disease is a drug taken to maintain health and prevent or delay the onset of Parkinson's disease or Parkinson's-like disease. For example, such subject can be administered a compound that inhibits, decreases, reverses, or prevents α-synuclein fibrillation and/or aggregation as a prophylactic measure. In other embodiments, such subject can be given gene therapy. For example, an adeno-associated virus can be used to transport a gene that codes for the enzyme glutamic acid decarboxylase (GAD) into the neurons of the subthalamic nucleus. The gene prompts these subthalamic cells to produce gamma-aminobutyric acid (GABA), the brain's primary inhibitory neurotransmitter, which decreases the activity in the subthalamic nucleus, a brain area that tends to be extremely overactive in Parkinson's patients, thereby restoring the normal motor function. Other experimental techniques for treatment of neurodegenerative disorders include stem cells transplants and upregulation of a molecule that prevents neurodegeneration.

EXAMPLES

Example 1

Subjects and Archived Data: Archived data of 45 individuals diagnosed with RBD in addition to 45 age and gender-matched insomnia patients as control subjects are analyzed. Complete, one-night polysomnography evaluations would have already been completed in all of these individuals. The data from these studies are stored in an electronically retrievable and analyzable form, including continuous EKG recordings. In alternative embodiments, data are obtained from subjects screened and diagnosed for RBD.

Diagnosis and inclusionary criteria: All charts and sleep recordings from this cohort of RBD patients is first subjected to a structured and systematic restoring to confirm a diagnosis of RBD. The International Classification of Sleep Disorders, Second edition (ICSD-2) is used as the diagnostic criteria for RBD. Those subjects meeting the diagnostic criteria after re-scoring are included in this project.

Control subjects: Polysomnograms from age- and sex-matched patients with insomnia, who do not have any other conditions that could affect HRV (neurodegenerative or cardiovascular diseases, diabetes, certain medication etc.), are selected as control subjects.

Data retrieval and analysis: Data are collected using the 'Sandman Elite®' sleep diagnostic system. This system collects patient electrophysiological data, including EKG, and saves them digitally on a computer. All data are de-identified of personal or confidential information. REM sleep portions of the EKG are selected for each subject (RBD patients and insomnia controls) since this is the sleep phase when there is the most variability in heart rate; furthermore it is the time during sleep that most resembles wakefulness physiologically. A five minute EKG segment under stable conditions (stable breathing and no leg movements) is visually identified and the beat-to-beat (R-R) interval data for this period is manually selected and saved for further HRV analysis.

HRV Analysis tools: The R-R interval is used as the input to a free software program developed for the study of HRV by the University of Kuopio, Finland. This program calculates all of the time and frequency domain parameters commonly used in HRV analysis. Graphical representations in the form of Poincaré plots and parametric and non-parametric spectral estimates are also generated.

Parameters to be evaluated: HRV is influenced by both the sympathetic and parasympathetic nervous system and can be assessed with time and frequency domain methods. Time domain measures of HRV used are the mean, the standard deviation of R-R intervals (SDNN), and the percentage number of consecutive RR intervals differing by more than 50 msec (pNN50).

In the frequency domain, Power Spectral Density of the three frequency bands of HRV are Very Low Frequency, VLF (0-0.04 Hz), Low Frequency, LF (0.04-0.15 Hz), High Frequency, HF (0.15-0.4 Hz). LF/HF ratio is also calculated. The HF band is related to respiration and considered to be parasympathetically mediated. LF is influenced both by the sympathetic and parasympathetic components. VLF involves thermoregulatory and peripheral vascular mechanisms. The nonlinearities in HRV are graphically represented by the Poincaré plot which shows the correlation between consecutive RR intervals.

Statistical Analysis: Statistical analysis is performed on the two groups (RBD patients and controls). The various time and frequency parameters are analyzed for their statistical significance using a parametric method. Based on literature values of R-R variability in normal subjects, RBD and Parkinson's disease or Parkinson's-like disease patients, a power analysis yielded a sample size of 20 subjects for each group to be adequate to achieve 80% power for all variables. Based on alpha of 0.05 and our sample size of 45 subjects in each group, even if only half of the subjects have pre-motor Parkinson's disease or Parkinson's-like disease, there is enough statistical power to detect differences in the two groups.

A statistically significant decrease is observed in HRV in RBD patients compared to insomnia controls. In addition, the analysis allows the search for other cardiac variables that might separate RBD patients from controls. Patients with insomnia are used as controls, as this group presents the least deviation in HRV from normal subjects. As a secondary analysis, RBD patients are compared against standardized data from the literature. In order to eliminate any data transfer issues, a "proof of principle" assessment was conducted by going step by step through the entire process of data transfer and analysis with data from three randomly selected subjects, and have successfully completed the process in all three instances. One of these patients showed a near complete loss of HRV as expected (FIG. 1). The figure shows the scatter plot (the Poincaré plot) of the current R-R interval ($RRI_{n+1}$ (s)) plotted against the preceding R-R interval ($RRI_n$ (s)) for a control subject (top) as well as that for an RBD patient (bottom). The scatter for the control subject is large indicating a large R-R variability. This denotes a balanced autonomic function. The scatter for the RBD patient is minimal, indicating very little variability in R-R intervals. This denotes autonomic denervation similar to that of a heart transplant patient. Thus, in this particular RBD patient the autonomic denervation is severe.

EKGs during quite wakefulness are also obtained for comparative analysis.

Example 2

Assessment of Heart Rate Variability During Wakefulness in Patients with RBD

A retrospective case-control study of 11 RBD patients and 11 control subjects without RBD was performed. Heart rate variability (HRV) analysis was performed from the R-R intervals during wakefulness. These were obtained from pre-sleep segment of electrocardiogram (EKG) channel of one night polysomnography.

Methods:

Subjects and Archived Data: The EKG tracings of patients undergoing polysomnography (PSG) from the year 2000 through 2008 were analyzed. All patients diagnosed with RBD during this period were identified through a search of the medical records. Age and gender-matched patients undergoing PSGs for insomnia during the same period were identified and used as control subjects.

Diagnosis and inclusionary criteria: All clinic patient charts and sleep recordings from this cohort of RBD patients were systematically rescored at the SSDC to confirm a diagnosis of RBD. The International Classification of Sleep Disorders, Second edition (ICSD-2) was used as the diagnostic criteria for RBD. Only RBD subjects who showed PSG abnormality typical of RBD after rescoring and also exhibited clinical symptoms compatible with dream-enacting behavior were included. Thus, those presenting subclinical RBD (typical PSG findings but no reported clinical symptoms) were, excluded. Other exclusionary factors included cardiovascular disease, significant arrhythmias, diabetes, other neurological disorders, or other sleep disorders such as narcolepsy, or current use of medications that are known to influence autonomic function. RBD patients=11 (mean age 63.27±7.46 years).

Control subjects: Because polysomnogram (PSG) from a normal control population were unavailable, polysomnograms from age- and sex-matched patients with insomnia evaluated at SSDC, who did not have any other conditions that could affect HRV, were selected as the control subjects. Although not selected from the general population, subjects with insomnia are not typically known to have associate neurological disease and/or autonomic dysfunction. Therefore, this group was very close in cardiac autonomic function during wakefulness to that of normal individuals. Eleven control subjects (7 men and 4 women) were included in the study (mean age 59.45±8.66).

Data retrieval and analysis: All data were originally collected and stored using the 'Sandman Elite®' (Sandman Elite Sleep Diagnostic Software User's manual) sleep diagnostic system at the SSDC. This system collects a wide variety of electrophysiological data, including EKG, and saves them digitally on a computer. Data from PSG recordings of individuals with iRBD and controls meeting inclusion/exclusion criteria were de-identified by SSDC personnel and provided to the Parkinson's Institute (TPI) for analysis. One night polysomnogram (PSG) recordings were obtained. For the purpose of analysis, a period of data when the subjects were awake, i.e. before sleep onset, was required. In order to obtain a data segment during wakefulness, a period was identified on the polysomnogram that was after bio-calibration but before occurrence of one of the sleep stages, thus ensuring that all data analyzed were well before sleep onset. A 5-minute portion of the EKG during wakefulness and under stable conditions (stable breathing and no leg movements) was then visually identified during this period for each subject (RBD patients and insomnia controls). Any ectopic beats that occurred were manually removed and the beat-to-beat (R-R) interval data for this period was saved for further HRV analysis.

HRV Analysis tools: The normal to normal (i.e. those resulting from sinus node depolarization) R-R interval was used as the input to a free software program developed for the study of HRV by the University of Kuopio, Finland by Niskanen et al. This program was used to calculate all of the time and frequency domain parameters commonly used in HRV analysis. Graphical representations in the form of Poincaré plots and parametric and non-parametric spectral estimates were also computed.

Parameters evaluated: HRV is an easily derived measure of cardiac autonomic activity. It is a reliable quantitative marker of autonomic nervous system activity and can be assessed with time and frequency domain methods. HRV can be quantified in terms of various measures that have been well established to be influenced by either the sympathetic or parasympathetic nervous system or is an indicator of sympathovagal balance.

One simple way of evaluating HRV is by the time domain measures. In this example, the standard deviation of R-R intervals (SDNN), the standard deviation of the heart rate (SDHR), the root mean square difference of successive RR intervals (RMSSD), and the percentage number of consecutive RR intervals differing by more than 50 msec (pNN50) were used. SDNN indicates the cyclic components responsible of variability in the given period of measurement and is equivalent to the total spectral power. RMSSD and pNN50 estimate high frequency variations in the heart rate and correlate well with the HF component of spectral power.

The NN intervals can also be represented as a geometric pattern, for example as Poincaré plots, a graphical representation of the relationship between consecutive RR intervals, where an RR interval is plotted against the preceding RR interval. The short term HRV (SD1) and the long term HRV (SD2) were obtained from the plots. SD1 reflects mainly respiratory sinus arrhythmia and thus correlates well with the HF component. Another geometric method is sample density distribution of the NN intervals. RR triangular index (the integral of the density distribution) and the triangular interpolation of NN, TINN (baseline width of the distribution measured as a base of a triangle approximating the NN interval distribution) were also calculated.

In the frequency domain, Power Spectral Density of the three frequency bands of HRV, namely Very Low Frequency, VLF (0-0.04 Hz), Low Frequency, LF (0.04-0.15 Hz), High Frequency, HF (0.15-0.4 Hz) were calculated. The HF band is related to respiration and considered to be parasympathetically mediated. LF is influenced both by the sympathetic and parasympathetic components. The LF/HF ratio was also calculated and may indicate sympathovagal balance. VLF is thought to involve thermoregulatory and peripheral vascular mechanisms. Non-parametric methods using fast Fourier transforms (FFT) were employed. Total Power refers to total power of all frequency bands.

Statistical Analysis: All time and frequency domain HRV parameters were tested for their statistical significance between RBD patients and control subjects. An unpaired student's t-test was used for statistical analysis. A p value of ≤0.05 was considered statistically significant. Results:

Patient Selection: Medical record review identified 35 individuals with a clinical diagnosis of RBD. After rescoring and chart review, 24 cases were excluded based on the exclusion criteria outlined above. The reasons for exclusion included lack of clinical symptoms i.e. subclinical RBD (4), other neurological and cardiovascular disorders (15), liver transplant (1), diabetes (1), and arrhythmias (3). The remaining 11 cases were included in the study and consisted of 9 men and 2 women (mean age 63.27±7.46 years).

Heart rate variability analysis: HRV as measured by both time domain and spectral measures varied significantly between the control group and the patients with RBD (see Table 1). Several time domain, frequency domain and geometric measures showed significantly attenuated HRV in the RBD patients compared to the control group.

TABLE 1

HRV parameters between control and RBD groups

| | RBD patients | Control group | p value |
| --- | --- | --- | --- |
| RR (ms) | 936.36 ± 92.77 | 948.55 ± 179.59 | NS |
| SDNN (ms) | 18.09 ± 6.39 | 28.73 ± 11.15 | p < 0.01 |
| HR (bpm) | 64.75 ± 5.94 | 65.44 ± 11.56 | NS |
| SDHR (bpm) | 1.84 ± 0.75 | 2.65 ± 1.04 | p < 0.05 |
| RMSSD (ms) | 16.98 ± 5.89 | 27.13 ± 12.54 | p < 0.03 |
| pNN50 (%) | 2.16 ± 2.12 | 9.71 ± 10.23 | p < 0.03 |
| SD1 (ms) | 12.35 ± 4.75 | 19.6 ± 9.03 | p < 0.03 |
| SD2 (ms) | 44.45 ± 20.07 | 68.91 ± 32.04 | p < 0.05 |
| RR triangular index | 0.04 ± 0.01 | 0.05 ± 0.02 | p < 0.04 |
| TINN (ms) | 96.36 ± 32.13 | 150.91 ± 62 | p < 0.02 |
| VLF ($ms^2$) | 11.09 ± 7.75 | 22.64 ± 17.72 | p < 0.06 |
| LF ($ms^2$) | 102 ± 69.57 | 349.91 ± 294.25 | p < 0.01 |
| LF (nu) | 61.64 ± 16.43 | 69.75 ± 19.85 | NS |
| HF ($ms^2$) | 48.91 ± 30.27 | 133.73 ± 112.2 | p < 0.03 |
| HF (nu) | 38.36 ± 16.43 | 30.25 ± 19.85 | NS |
| Total Power ($ms^2$) | 162 ± 98.15 | 506.27 ± 395.32 | p < 0.01 |
| LF/HF | 2.15 ± 1.38 | 3.3 ± 1.97 | NS |

Figure 2:
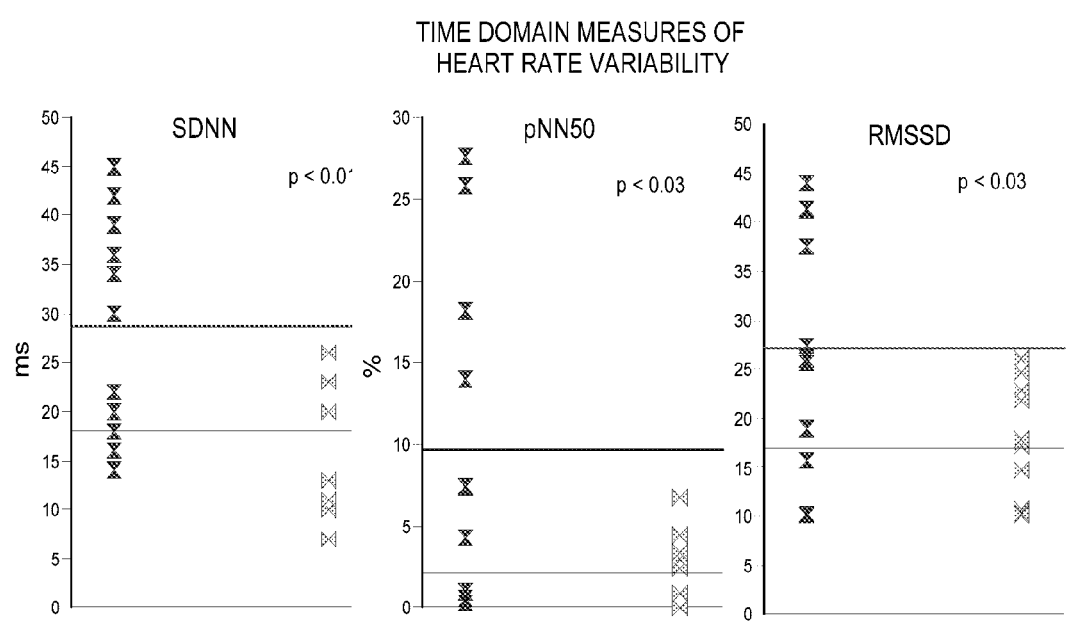
FIG. 2 depicts time domain measures HRV between control subjects and patients with RBD. The various measures are a. SDNN—standard deviation of RR intervals b RMSSD—the root mean square difference of successive RR intervals c. pNN50—percentage of the number of pairs of adjacent normal RR intervals differing by more than 50 ms. SDNN ($p<0.01$), RMSSD ($p<0.03$) and pNN50 ($p<0.03$) are all significantly less for the RBD patients compared to control subjects. The horizontal lines indicate the mean values. Notice that for all time domain parameters, all data for RBD patients is below the average line for the control subject.

Data are presented as mean ± SD.
Parameters showing statistical significance are shown in bold The standard deviation of RR interval, SDNN ($p<0.01$) and heart rate, SDHR ($p<0.05$), were lower in RBD than in the control group. RBD patients also had significantly lower RMSSD ($p<0.03$) and pNN50 ($p<0.03$) than the control subjects (FIG. 2). The RR interval and heart rate were not significantly different between the groups.

Standard deviations of the Poincaré plots namely, SD1 (perpendicular to the line of identity and SD2 (along the line of identity) were calculated. SD1 describes the short term variability caused mainly by respiratory sinus arrhythmia. SD2 denotes long term variability. Both SD1 (p<0.03) and SD2 (p<0.05) are lower in RBD compared to the control group. The geometric measures, RR triangular index (p<0.04) and TINN (p<0.01) are also significantly less in the RBD patients compared to the control group (Table 1).

Figure 3:
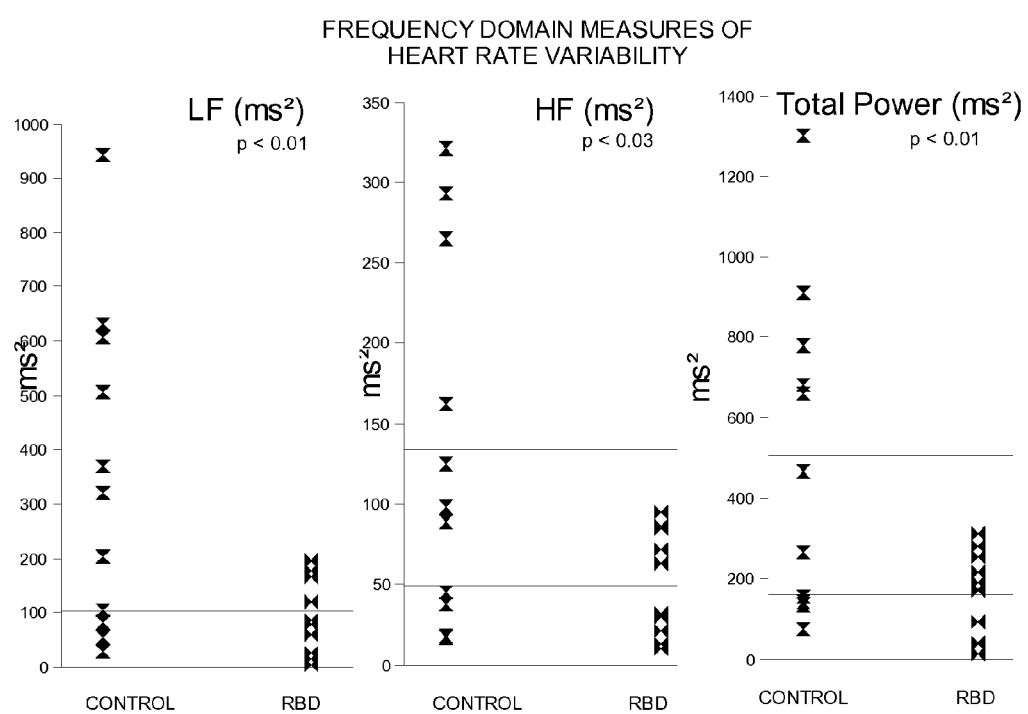
FIG. 3 depicts frequency domain measures of HRV as calculated by Fast Fourier Transform (FFT) between control subjects and patients with RBD. The measures shown are: a.) VLF ($ms^2$)—spectral power in the very low frequency band; b.) LF ($ms^2$)—Low Frequency power; c.) HF ($ms^2$)—High Frequency power; and d.) Total power ($ms^2$)—total power of VLF, LF and HF bands. The VLF ($p<0.04$), LF ($p<0.01$), HF ($p<0.03$) and total spectral power ($p<0.01$) all were significantly lower in the RBD patient group compared to the control group.
Figure 4:
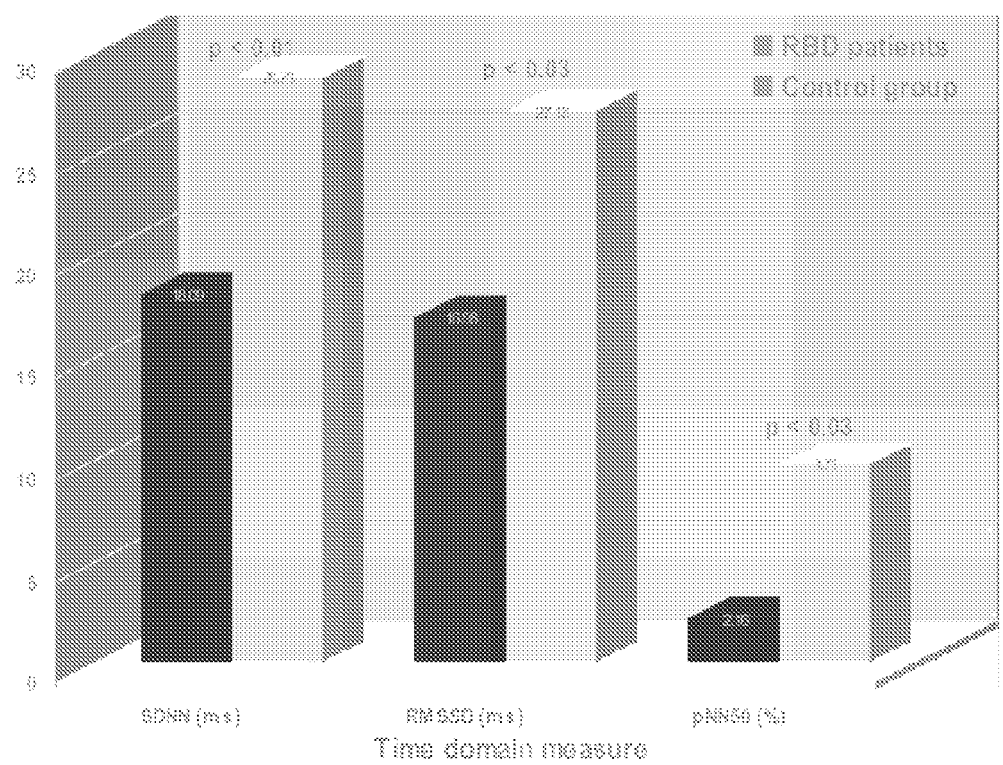
FIG. 4 shows time domain measures of HRV between RBD patients and the control group.
Figure 5:
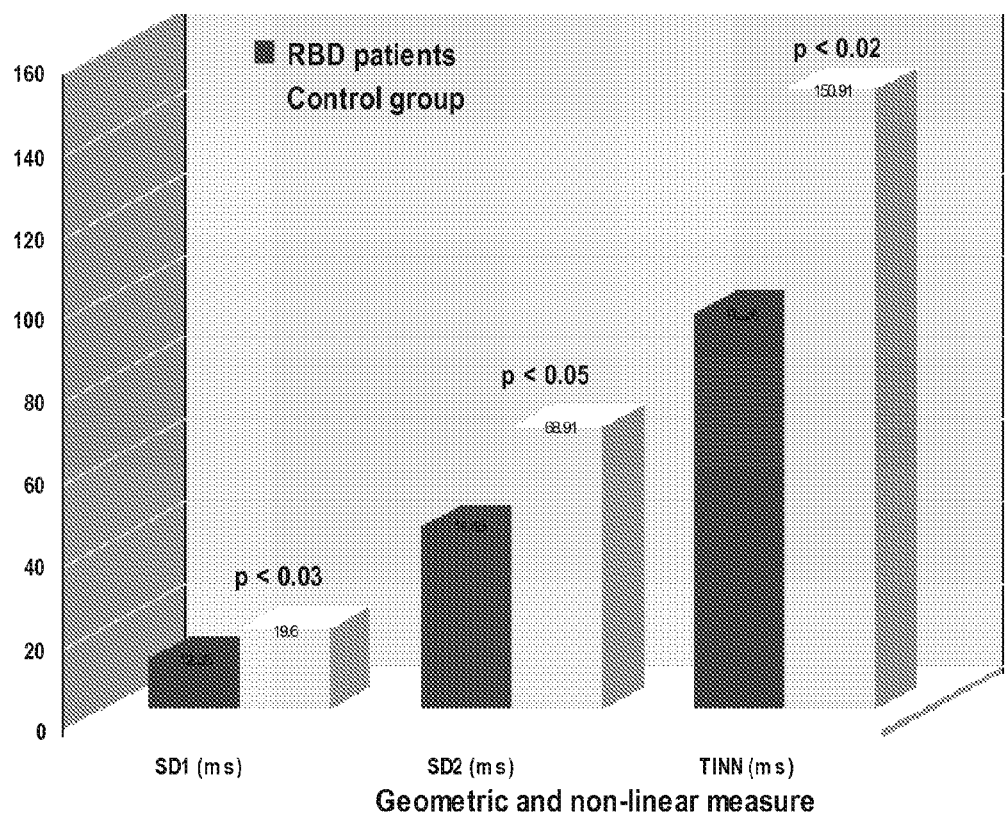
FIG. 5 shows geometric/non-linear measures of HRV between RBD patients and the control group.
Figure 6:
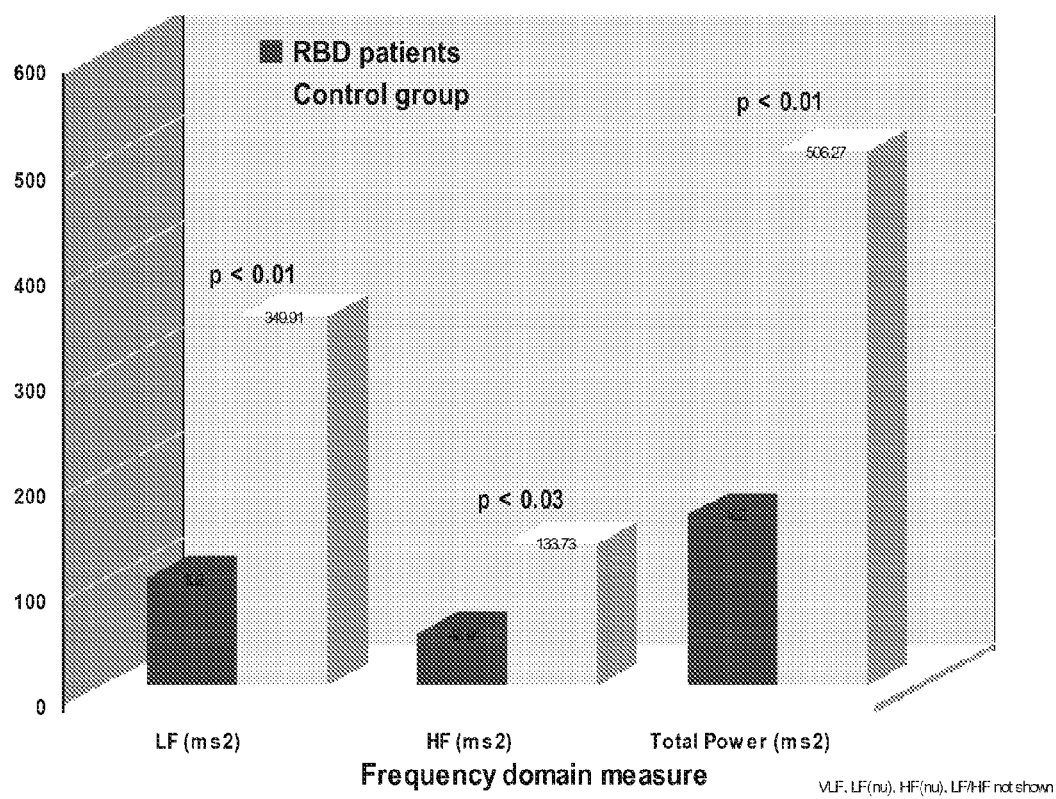
FIG. 6 shows frequency domain measures of HRV between RBD patients and the control group.

All the spectral power components proved to be lower in patients with RBD vs. the control group. Low Frequency (LF) power (p<0.01), High Frequency (HF) power (p<0.03) and Total Spectral Power (p<0.01) were attenuated in RBD patients. However, the normalized units (power in a band divided by the total power-power of VLF) failed to reach a significant difference between the groups. Although the VLF power and LF/HF ratio also indicated a trend toward a much lower value in the RBD group, it was not significantly different between RBD and control groups as indicated in Table 1. Similar to the time-domain measures, the spectral measures are much lower than the mean for the control group (FIG. 3).

Example 3

Assessment of Heart Rate Variability (HRV) During Wakefulness in Patients with RBD Methods: Data from polysomnograms performed between the years 2000 to 2008 in 10 RBD patients and 10 age- and sex-matched controls were retrieved and the pre-sleep segments of EKG channel analyzed for changes in HRV.
Results:

TABLE 2

HRV parameters between control and RBD groups

| | RBD patients | Control group | p value |
|---|---|---|---|
| RR (ms) | 941.5 ± 95.8 | 945.3 ± 188.98 | NS |
| SDNN (ms) | 17.6 ± 6.49 | 29.8 ± 11.14 | p < 0.01 |
| HR (bpm) | 64.437 ± 6.14 | 65.84 ± 12.1 | NS |
| SDHR (bpm) | 1.784 ± 0.75 | 2.77 ± 1.01 | p < 0.03 |
| RMSSD (ms) | 16.21 ± 5.62 | 27.27 ± 13.20 | p < 0.03 |
| pNN50 (%) | 2.03 ± 2.18 | 10.24 ± 10.61 | p < 0.03 |
| SD1 (ms) | 11.81 ± 4.11 | 19.73 ± 9.50 | p < 0.03 |
| SD2 (ms) | 43.89 ± 20.93 | 70.26 ± 33.44 | p < 0.05 |
| RR triangular index | 0.038 ± 0.01 | 0.052 0.016 | p < 0.03 |
| TINN (ms) | 92 ± 30.43 | 157 ± 61.78 | p < 0.01 |
| VLF ($ms^2$) | 11.2 ± 8.12 | 24.6 ± 17.37 | p < 0.04 |
| LF ($ms^2$) | 104.3 ± 72.56 | 382.1 ± 289.02 | p < 0.01 |
| LF (nu) | 62.97 ± 16.66 | 74.91 ± 10.62 | p < 0.08 |
| HF ($ms^2$) | 45.3 ± 29.40 | 134.6 ± 118.22 | p < 0.03 |
| HF (nu) | 37.03 ± 16.66 | 25.09 ± 10.62 | p < 0.08 |
| Total Power ($ms^2$) | 160.8 ± 102.85 | 541.3 ± 398.30 | p < 0.01 |
| LF/HF | 2.26 ± 1.39 | 3.60 ± 1.77 | p < 0.08 |

Data are presented as mean ± SD.
Parameters showing statistical significance, shown in bold A wide variety of HRV measures, including standard deviation of N-N intervals (SDNN) and heart rate (SDHR), root mean square difference of successive RR intervals (RMSSD) percentage of number of pairs of adjacent RR intervals differing by more than 50 ms (pNNSO), short term HRV (SD1) and long term HRV (SD2) obtained from the Poincaré plot, RR triangular index, triangular interpolation of NN (TINN), spectral powers in the Very Low Frequency (VLF), Low Frequency (LF) and High Frequency (HF) bands as well as Total Spectral Power, were significantly lower in RBD patients than controls (Table 2). The LF/HF ratio, normalized LF (LF nu) and HF (HF nu) also showed a trend in the same direction.

Example 4

EKG can be Used to Identify Prodromal Parkinson's Disease and/or Parkinson's-Like Disease A person experiencing symptoms of RBD such as loss of normal voluntary muscle atonia during REM sleep, associated with complex behavior while dreaming visits the doctor's office and is advised to undergo at least about a 5-minute EKG. The EKG measures the person's HRV. The algorithm of the present invention is applied to the person's EKG results to assess his HRV and the associated variables, and then compares the person's HRV to the standard HRV range which is indicative of Parkinson's disease or Parkinson's-like disease. The person's EKG results fall into the EKG range predetermined to be indicative of Parkinson's disease or Parkinson's-like disease, suggesting that this person may have prodromal/pre-motor Parkinson's disease or Parkinson's-like disease. But the person does not experience any motor symptoms on the USPRDS and HY scales at this stage.

The person subsequently undergoes a genetic testing for Parkinson's disease. The person is screened for a mutation in the following genes: leucine-rich repeat kinase 2 (LRRK2), α-synuclein (SNCA), parkin (PRKN), ubiquitin C-terminal hydrolase L1 (UCH-L1), oncogene DJ-1 gene, PTEN-induced protein kinase 1 (PINK1), and microtubule-associated protein tau (MAPT). The mutations include substitution, deletion, insertion, duplication, triplication or a combination thereof. The person further undergoes brain imaging. He takes both PET scan and MRI. The genetic screening results indicate that this person has mutations the LRRK2 gene, and the brain imaging results also suggest that this person lowered activity in certain brain regions. Thus, the method of the present invention can be used to diagnose premotor or prodromal Parkinson's disease or Parkinson's-related disease, at an early stage, prior to the onset of diagnosable motor symptoms.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A method of detecting an increased risk of developing Parkinson's disease or Parkinson's-like disease indicated by a loss of standard deviation of heart rate (SDHR), said method comprising:
   a) selecting a subject that does not exhibit motor symptoms indicative of Parkinson's disease or Parkinson's-like disease; b) obtaining 5 or fewer minutes of heart rate data;

c) determining a SDHR of said subject from the heart rate data;
d) detecting the increased risk for developing Parkinson's disease or Parkinson's-like disease if said SDHR of said subject is less than a control SDHR; and
e) taking a sample for genetic testing, if the increased risk for developing Parkinson's disease or Parkinson's-like disease has been detected in said subject in step d).

2. The method of claim 1, wherein the subject is in a wakeful state or awake while measuring heart rate.

3. The method of claim 1, further comprising treating said subject.

4. The method of claim 1, wherein the subject scores a 0 on a scale selected from a Unified Parkinson's Disease Rating Scale (UPDRS) and a Hoehn and Yahr scale.

5. The method of claim 1, wherein the control SDHR is obtained from one or more healthy subjects.

6. The method of claim 1, wherein the control SDHR is obtained from one or more subjects selected from a subject that is not diagnosed with Parkinson's disease or Parkinson's-like disease.

7. The method of claim 1, wherein the subject does not exhibit motor symptoms indicative of Parkinson's Disease or Parkinson's like disease as assessed by a scale selected from the Hoehn and Yahr Scale and the Unified Parkinson's Disease Rating Scale (UPDRS).

8. The method of claim 1, wherein the SDHR of said subject is below the average for the control SDHR.

9. A method of detecting an increased risk of developing Parkinson's disease or Parkinson's-like indicated by a loss of standard deviation of heart rate (SDHR), said method comprising:
a) selecting a subject that does not exhibit motor symptoms indicative of Parkinson's disease or Parkinson's-like disease as assessed by the Hoehn and Yahr Scale or the Unified Parkinson's Disease Rating Scale (UPDRS);
b) obtaining 5 or fewer minutes of heart rate data from said subject;
c) determining a SDHR of said subject from the heart rate data;
d) detecting the increased risk for developing Parkinson's disease or Parkinson's-like disease if said SDHR of said subject is less than a control SDHR, and
e) taking a sample for genetic testing, if the increased risk for developing Parkinson's disease or Parkinson's-like disease has been detected in said subject in step d).

* * * * *